United States Patent [19]

Braun et al.

[11] 4,229,556

[45] Oct. 21, 1980

[54] REACTIVE OLIGOMERS AS CURING AGENT FOR UNSATURATED POLYESTER

[75] Inventors: Dietrich Braun, Darmstadt-Arheilgen; Klaus Titzschkau, Darmstadt, both of Fed. Rep. of Germany

[73] Assignee: Bayer Aktiengesellschaft, Fed. Rep. of Germany

[21] Appl. No.: 5,770

[22] Filed: Jan. 23, 1979

[30] Foreign Application Priority Data

Jan. 27, 1978 [DE] Fed. Rep. of Germany ....... 2803494
Feb. 13, 1978 [DE] Fed. Rep. of Germany ....... 2805904

[51] Int. Cl.² .............................................. C08L 67/06
[52] U.S. Cl. ..................................... 525/445; 525/25; 525/447; 525/437; 528/362
[58] Field of Search ...................... 260/862, 864, 870; 528/362; 525/25, 445, 447

[56] References Cited

FOREIGN PATENT DOCUMENTS 810222 3/1959 United Kingdom.

OTHER PUBLICATIONS

Osterreichische Kunstoff–Zeitschrift, Jul./Aug., 1977, p. 110, col. 2, last paragraph, p. 111, first col., first paragraph.

*Primary Examiner*—Harold D. Anderson
*Attorney, Agent, or Firm*—Connolly and Hutz

[57] ABSTRACT

Reactive oligomers obtainable by reacting α-substituted acrylic acid derivatives and tetra-aryl succinic acid dinitriles do excellently work as non-peroxidic initiators for curing radically polymerizable compounds and compositions, particularly unsaturated polyester resins.

7 Claims, No Drawings

REACTIVE OLIGOMERS AS CURING AGENT FOR UNSATURATED POLYESTER

The present invention relates to reactive oligomers obtainable from α-substituted acrylic acid derivatives and tetra-aryl succinic acid nitriles, to a process for their production and to their ability of initiating radical polymerization reactions, particularly the curing of unsaturated polyester resins.

The reactive oligomers provided by the present invention are presented by the following formula

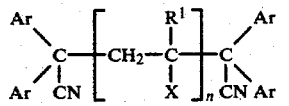

wherein
Ar is an optionally substituted aryl radical,
$R^1$ is an alkyl group,
X is a CN-group or a $COOR^2$-group in which $R^2$ is H or an alkyl group containing from 1 to 12 carbon atoms, and
n a number of from 1 to 20.

Typical examples of substituents which may be present on the aryl group are one or more alkyl groups and halogen atoms, and it is preferred that the group $R^1$ is an alkyl group having from 1 to 4 carbon atoms.

Preferred reactive oligomers are those of formula I, wherein
Ar is a phenyl, a $C_1$-$C_4$ alkyl phenyl or a chlorophenyl group;
$R^1$ is a methyl group,
$R^2$ is a methyl or ethyl group,
X is $COOR^2$ and
n a number from 2 to 6.

Particularly preferred reactive oligomers are those of tetraphenyl succinic acid dinitrile and methyl methacrylate containing from 2 to 6 methyl methacrylate residues.

The oligomers according to the present invention may be obtained from the corresponding α-substituted acrylic acid derivatives and the tetra-aryl succinic acid dinitriles. The α-substituted acrylic acid derivatives used have the following formula:

wherein $R^1$ and X are as hereinbefore defined.
Methyl methacrylate is particularly preferred.
The tetra-aryl succinic acid dinitriles used have the formula:

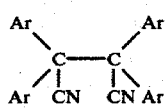

Accordingly, it is also an embodiment of the present invention to provide a process for the preparation of oligomers of formula (I)

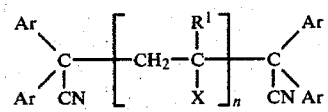

wherein Ar is an optionally substituted aryl group, $R^1$ is an alkyl group, X is a CN group or a group $COOR^2$ in which $R^2$ is H or an alkyl group having from 1 to 12 carbon atoms and n is a number from 1 to 20 which comprises reacting a compound of formula (II)

wherein $R^1$ and X are as hereinbefore defined with a compound of formula (III)

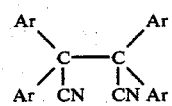

wherein Ar is as hereinbefore defined at a temperature of from 60° to 100° C.

To produce the oligomers, the tetra-aryl succinic acid dinitrile can be dissolved or suspended in an α-substituted acrylic acid derivative and the mixture can then be heated. The reaction may also be carried out in the presence of a diluent, which is inert to the reactants. Preferred inert diluents are optionally halogenated aromatic hydrocarbons, such as benzene, chlorobenzene, xylene and toluene.

The quantity of tetra-aryl succinic acid dinitrile used, based on the α-substituted acrylic acid derivative, is determined by the required degree of oligomerization of the reactive oligomer I. The greater the quantity of tetra-aryl succinic acid dinitrile used, based on the acrylic acid derivative, the lower is the degree of oligomerization.

The quantity of tetra-aryl succinic acid dinitrile used may amount to from 40% by weight to 0.05% by weight, based on α-substituted acrylic acid derivative. In cases where the reaction is carried out in the absence of a diluent, i.e. in cases where an excess of α-substituted acrylic acid derivative is used as the reaction medium, this corresponds to degrees of oligomerization of from about 2 to about 20. If small quantities of tetra-aryl succinic acid dinitrile (up to about 1% by weight, based on the α-substituted acrylic acid derivative) are used, more tetra-aryl succinic acid dinitrile may be added to the mixture on completion of oligomerization, resulting in the formation of more oligomer. This may be repeated for as long as new oligomer dissolves in the α-substituted acrylic acid derivative. In most cases, a practical limit lies at an approximately 20 to 30% conversion of the α-substituted acrylic acid derivative.

The oligomerization reaction takes place at temperatures of from about 60° C. to about 100° C. The oligomers may be isolated by precipitation with suitable precipitants (petroleum ether) or even by removing the residual monomers by distillation.

The reactive oligomers obtained are generally substances which are solid at room temperature. They are unaffected by air and light, are readily soluble in a number of vinyl monomers and solvents (alcohols, aromatic hydrocarbons, chloroform, acetone, tetrahydrofuran, dimethyl formamide) and are insoluble in water and petroleum ether. Their most outstanding property is that they are themselves reactive, i.e. they show radical-forming properties. For this reason, they may be used for the radical curing of polymerizable compounds and compositions, particularly unsaturated polyester resins. Even more surprising is the fact that they are capable of existing at all and are actually stable because tetraphenyl succinic acid dinitrile is known as an initiator for the polymerization of methylenic monomers. Accordingly, polymers would normally be expected to form in the presence of this initiator. Suprisingly, this is not the case with the α-substituteed acrylic acid derivatives according to the invention. Oligomers are formed even when the monomer is present in a large excess.

Typical substances in which polymerization can be initiated by the reactive oligomers according to the invention, i.e. all the compounds or mixtures which can be copolymerized by free radical mechanisms, include conjugated dienes, such as butadiene, isoprene and chloroprene; vinyl chloride and vinylidene chloride; aromatic vinyl compounds, such as styrene and divinylbenzene; vinyl esters, especially vinyl acetate and vinyl propionate; vinyl ethers, such as vinyl propyl ether and vinyl isobutyl ether; acrylic acid and methacrylic acid and their derivatives, such as esters, especially with aliphatic alcohols with 1 to 5 C-atoms, nitriles, amides and the like; di-(vinylphenyl)-carbonates; diallyl phthalate, diallyl carbonate and diallyl fumarate; di-(allylphenyl) carbonates; polyol-poly(meth) acrylates; and N,N'-methylene-bis-(meth)acrylamide.

Preferred substances whose polymerization can be initiated by the reactive oligomers according to the invention include acrylic and methacrylic acid derivatives, particularyl a. 2-hydroxyethyl acrylate,
    2-hydroxyethyl methacrylate,
    2-hydroxypropyl acrylate,
    2-hydroxypropyl methacrylate,
    4-hydroxybutyl acrylate and methacrylate;
b. styrene and methylmethacrylate;
c. ethyl acrylate, methyl acrylate, butyl acrylate, butyl methacrylate, 2-ethylhexyl acrylate, 2-ethylhexyl methacrylate;
d. acrylic acid, methacrylic acid and maleic monoesters having from 4 to 8 carbon atoms in the alcohol component;
e. glycidyl acrylate and methacrylate resp. their reaction products with saturated and/or unsaturated aliphatic and/or aromatic monocarboxylic acids;
f. methoxymethylacrylic acid amide and methoxymethyl methacrylic acid amide;
g. acrylonitrile.

The reactive oligomers according to the invention can, of course, be used for the preparation of block copolymers, e.g. from hydrophobic and hydrophilic segments.

Particularly preferred substances whose polymerization can be initiated by the reactive oligomers according to the invention are unsaturated polyester resins, that is to say the solutions of α,β-ethylenically unsaturated polyesters in monomeric vinyl or vinylidene compounds which are copolymerizable therewith.

The polyester/monomer ratio is generally in the range of from 30/70 to 70/30 parts by weight. α,β-Ethylenically unsaturated polyesters in the sense of the invention are the customary polycondensation products of at least one α,β-ethylenically unsaturated dicarboxylic acid with, as a rule, 4 or 5 C-atoms, or the ester-forming derivatives thereof, for example the anhydrides thereof, optionally mixed with up to 200 mol %, relative to the unsaturated acid components, of at least one aliphatic saturated dicarboxylic acid with 4–10 C-atoms or at least one cycloaliphatic and/or aromatic dicarboxylic acid with 8 to 10 C-atoms, or the ester-forming derivatives thereof, with at least one polyhydroxy compound, especially a dihydroxy compound, with 2–8 C-atoms, that is to say polyesters such as those described by J. Björksten et al., "Polyesters and their Applications", Reinhold Publishing Corp., New York 1956.

Examples of unsaturated dicarboxylic acids or their derivatives, which are preferably to be used are maleic acid or maleic anhydride and fumaric acid. However, it is also possible to use, for example, mesaconic acid, citraconic acid, itaconic acid or chloromaleic acid. Examples of the aliphatic saturated, cyclo-aliphatic and aromatic dicarboxylic acids, or their derivatives, which are to be used are phthalic acid or phthalic anhydride, isophthalic acid, terephthalic acid, hexa- or tetra-hydrophthalic acid or their anhydrides, endomethylene-tetrahydrophthalic acid or its anhydride, succinic acid or succinic anhydride and succinic acid esters and succinic acid chlorides, adipic acid and sebacic acid. In order to prepare resins of low flammability it is possible to use, for example, hexachloroendomethylenetetrahydrophthalic acid, tetrachlorophthalic acid or tetrabromophthalic acid. Dihydric alcohols which can be employed are ethylene glycol, propane-1,2-diol, propane-1,3-diol, diethylene glycol, dipropylene glycol, butane-1,3-diol, butane-1,4-diol, neopentylglycol, hexane-1,6-diol, 2,2-bis-(4-hydroxycyclohexyl)-propane, bis-oxalkylated bisphenol A, perhydrobisphenol and others. Ethylene glycol, propane-1,2-diol, diethylene glycol and dipropylene glycol are preferably used.

Further modifications are possible by incorporating monohydric, trihydric and tetrahydric alcohols with 1–6 C-atoms, such as methanol, ethanol, butanol, allyl alcohol, benzyl alcohol, cyclohexanol and tetrahydrofurfuryl alcohol, trimethylolpropane, glycerol and pentaerythritol and also mono-, di- and tri-allyl ethers and benzyl ethers of trihydric and polyhydric alcohols with 3–6 C-atoms according to DE-AS (German Published Specification) No. 1,024,654, and also by incorporating monobasic acids, such as benzoic acid, or long-chain unsaturated fatty acids, such as oleic acid, linseed oil fatty acid and castor oil fatty acid.

The acid numbers of the polyesters are usually between 1 and 100 and preferably between 20 and 70, the OH-numbers are between 10 and 150 and preferably between 20 and 100 and the molecular weights $\overline{M}_n$, determined as a number-average, are between about 500 and 5,000 and preferably between about 1,000 and 3,000 (measured by vapour pressure osmometry in dioxane and acetone; in the case of differing values, the lower value is regarded as being correct).

Preferred vinyl and vinylidene compounds which can be copolymerized with the unsaturated polyesters are the unsaturated compounds which are customary in polyester technology and preferably carry α-substituted vinyl or vinylidene groups or β-substituted allyl groups, preferably styrene; however, for example, styrenes which are chlorinated and alkylated or alkenylated in the nucleus and in which the alkyl groups can contain 1-4 carbon atoms, for example vinyltoluene, divinylbenzene, α-methylstyrene, tert.-butylstyrene and chlorostyrenes; vinyl esters of carboxylic acids with 2-6 carbon atoms, preferably vinyl acetate; vinylpyridine, vinylnaphthalene, vinylcyclohexane, acrylic acid and methacrylic acid and/or their esters (preferably the vinyl, allyl and methallyl esters) with 1-4 carbon atoms in the alcohol component and their amides and nitriles, maleic anhydride, maleic acid half-esters and diesters with 1-4 carbon atoms in the alcohol component and maleic acid half-amides and diamides, or cyclic imides, such as N-methylmaleimide or N-cyclohexylmaleimide; and allyl compounds such as allylbenzene and allyl esters such as allyl acetate, phthalic acid diallyl ester, isophthalic acid diallyl ester, fumaric acid diallyl ester, allyl carbonates, diallyl carbonates, triallyl phosphate and triallyl cyanurate are also suitable.

The reactive oligomers according to the invention can also be used to initiate the curing of unsaturated polyesters which are free from copolymerizable vinyl or vinylidene compounds, i.e. so-called "air-drying" polyesters having β, γ-ethylenically unsaturated ether groups, generally in amounts of from 0.2 to 0.8 mol per 100 g of polyesters. Such polyesters are described, for example, in German patent specification No. 22 21 335.

The oligomers according to the invention are, in general, used in amounts of from 0.05 to 3, preferably 0.1 to 2, % by weight, calculated on the unsaturated polyester resin.

The polymerization reaction is started by heating a mixture of the substance to be polymerized and the reactive oligomer according to the invention above a definite start temperature which is easy to determine for a particular case. Curing of systems which can be polymerized by free radical mechanism is as a rule effected at between 60° and 200° C.

The reactive oligomers according to the invention resp. their secondary products have the advantage over the initiators of the prior art to decrease the polymerization shrinkage and not to bleed out after curing.

The polymers cured in the presence of the reactive oligomers according to the invention have a very good Shore hardness and excellent values with respect to impact strength and bending tests.

The Examples which follow illustrate the invention.

In the text which follows the parts indicated are parts by weight and the percentage data are given as percentages by weight.

EXAMPLE 1

10 g of tetraphenyl succinic acid dinitrile and 38.4 g of methyl methacrylate are heated under nitrogen to 90° C. in a 100 ml capacity three-necked flask equipped with a stirrer and a reflux condenser. A suspension of the dinitrile with methyl methacrylate is obtained because the dinitrile does not completely dissolve. After 6 hours, no more sediment is present, the oligomer of methyl methacrylate and tetraphenyl succinic acid dinitrile having dissolved in the excess monomer. After another hour, nothing can be precipitated with methanol from a sample taken from the reaction solution. Only after another 30 minutes it is possible to precipitate small quantities of polymethyl methacrylate, whereas virtually no more free tetraphenyl succinic acid dinitrile is present. The reaction is terminated by cooling to around 20° C. and the unreacted methyl methacrylate is distilled off in vacuo. Oligomer is extracted from the residue with methanol and is obtained in pure form through concentration by evaporation. Yield 17.2 g; degree of oligomerization 2.8.

EXAMPLE 2

106 g of tetraphenyl succinic acid dinitrile and 94 g of methyl methacrylate are heated under nitrogen to 90° C. in a 250 ml capacity three-necked flask equipped with a stirrer and reflux condenser. The tetraphenyl succinic acid dinitrile dissolves completely. Further batches of 106 g of tetraphenyl succinic acid dinitrile are added at intervals of a few minutes, the following batch always being added after complete dissolution of the last batch. This operation is repeated 21 times. The reaction mixture is then worked up in the same way as in Example 1 except that, on this occasion, two oligomer fractions are obtained, one of which is soluble in methanol whilst the other is insoluble in methanol. The methanol-soluble fraction (9.3 g) has a degree of oligomerization of approximately 15 whilst the methanol-insoluble fraction (3.7 g) has a degree of oligomerization of approx. 30. A total of 13 g of oligomer having an average degree of oligomerization of 19.75 is obtained.

APPLICATION

A highly reactive unsaturated polyester resin comprising a maleic anhydride/phthalic anhydride/ propylene glycol polyester (molar ratio maleic anhydride/phthalic anhydride=70:30) and styrene, having a styrene content of 34%, a viscosity (determined at 20° C.) of 1250 cPoise and a double bond content of 0.22 equivalents fumaric acid per 100 g of polyester, is in the following referred to as polyester resin UPE.

The polyester resin UPE is admixed with the reactive oligomers in ratios listed below, and the obtained mixture is filled into test tubes having a diameter of 2 cm up to a height of 8 cm. The mixture is cured at a bath temperature of 110° C., the maximum temperature being determined by means of an iron/Konstantan thermoelement in accordance to DIN (German industrial standard) 16 945. Excellently cured products are thus obtained.

|  | Amount of Oligomers in % by weight, calculated on UPE | Maximum temperature [°C.] |
|---|---|---|
| Oligomer obtained in Ex. 1 | 0.5 | 209 |
|  | 1.0 | 211 |
|  | 1.5 | 216 |
| Oligomer obtained in Ex. 2 | 0.5 | 208 |
|  | 1.0 | 219 |
|  | 1.5 | 224 |

We claim:

1. In the process of curing a solution of an α-β ethylenically unsaturated polyester in at least one vinyl or vinylidene compound which is copolymerizable therewith, in the presence of a non-peroxidic initiator at a temperature of from 60°-200° C., said α-β ethylenically unsaturated polyester being the polycondensation product of at least one α-β ethylenically unsaturated dicarboxylic acid or ester-forming derivative thereof and at least one polyhydroxy compound, the improvement which comprises initiating polymerization with an oligomer of the formula

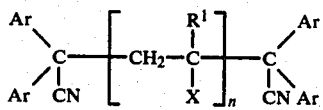

wherein Ar is aryl, $R^1$ is alkyl, X is CN or $COOR^2$ wherein $R^2$ is hydrogen or alkyl having 1 to 12 carbon atoms and n is a number from 1 to 20.

2. The process of claim 1 wherein Ar is aryl substituted with at least one alkyl moiety or with halogen.

3. The process of claim 1 wherein $R^1$ is alkyl having 1 to 4 carbon atoms.

4. The process of claim 1 wherein $R^1$ as methyl or ethyl.

5. The process of claim 1 wherein Ar is phenyl, alkylphenyl having 1 to 4 carbon atoms in the alkyl moiety or chlorophenyl.

6. The process of claim 1 wherein X is $COOR^2$.

7. The process of claim 1 wherein n is a number from 2 to 6.

* * * * *